(12) United States Patent
Baldauf et al.

(10) Patent No.: US 8,304,355 B2
(45) Date of Patent: Nov. 6, 2012

(54) ELASTIC COMPOSITE TAPE

(75) Inventors: Georg Baldauf, Laer (DE); Dieter Homoelle, Ochtrup (DE); Marcus Schoenbeck, Versmold (DE)

(73) Assignee: Nordenia Technologies GmbH, Grounau (DE)

( * ) Notice: Subject to any disclaimer, the term of this patent is extended or adjusted under 35 U.S.C. 154(b) by 511 days.

(21) Appl. No.: 12/413,647

(22) Filed: Mar. 30, 2009

(65) Prior Publication Data

US 2009/0252915 A1    Oct. 8, 2009

(30) Foreign Application Priority Data

Mar. 31, 2008 (EP) .................................. 08006233

(51) Int. Cl.
*D04B 21/00* (2006.01)
*D04B 21/14* (2006.01)
*D04B 1/18* (2006.01)
*B32B 3/10* (2006.01)
*B32B 1/06* (2006.01)
*B32B 38/04* (2006.01)
B32B 3/02 (2006.01)
B32B 5/04 (2006.01)
B32B 3/24 (2006.01)
B32B 5/08 (2006.01)
D04B 21/16 (2006.01)

(52) U.S. Cl. ........ 442/304; 428/113; 428/137; 428/138; 428/189; 428/190; 428/192; 428/193; 428/194; 428/195.1; 428/196; 428/201; 428/219; 442/312; 442/318

(58) Field of Classification Search .................... None
See application file for complete search history.

(56) References Cited

U.S. PATENT DOCUMENTS

| 2,620,480 | A | * | 12/1952 | Shea | ................... 2/111 |
| 4,536,441 | A | * | 8/1985 | Schmeer et al. | ............ 428/317.3 |
| 4,705,710 | A | | 11/1987 | Matsuda | .................... 428/92 |
| 4,935,287 | A | * | 6/1990 | Johnson et al. | ............... 428/198 |
| 5,695,849 | A | * | 12/1997 | Shawver et al. | .............. 428/131 |
| 5,762,623 | A | * | 6/1998 | Murphy et al. | .................. 602/75 |
| 6,663,584 | B2 | * | 12/2003 | Griesbach et al. | .............. 602/75 |
| 2004/0214494 | A1 | | 10/2004 | Murphyc | ....................... 442/149 |
| 2005/0130543 | A1 | * | 6/2005 | Baldauf | ........................ 442/394 |
| 2006/0247567 | A1 | * | 11/2006 | Baldauf et al. | .................... 604/1 |
| 2006/0257666 | A1 | | 11/2006 | Muslet | ....................... 428/411.1 |
| 2007/0234529 | A1 | * | 10/2007 | Middlesworth et al. | ........ 24/442 |
| 2008/0038983 | A1 | * | 2/2008 | Hagemann et al. | ........... 442/396 |

FOREIGN PATENT DOCUMENTS

JP      09075394        3/1997
WO    WO 2006008149 A1 *   1/2006

* cited by examiner

*Primary Examiner* — David Sample
*Assistant Examiner* — Jeff Vonch
(74) *Attorney, Agent, or Firm* — Andrew Wilford

(57) ABSTRACT

An elastic composite strip has a longitudinally elongated substrate strip having a pair of opposite faces and formed of an elastomer that is highly stretchable longitudinally but only limitedly or not stretchy at all transversely. A respective soft knit fabric cover strip that is highly stretchable longitudinally but only limitedly or not stretchy at all transversely extends longitudinally on each of the faces. Respective arrays of longitudinally spaced and transversely extending lines of adhesive are bonded to the faces and to filaments of the respective cover strips.

10 Claims, 2 Drawing Sheets

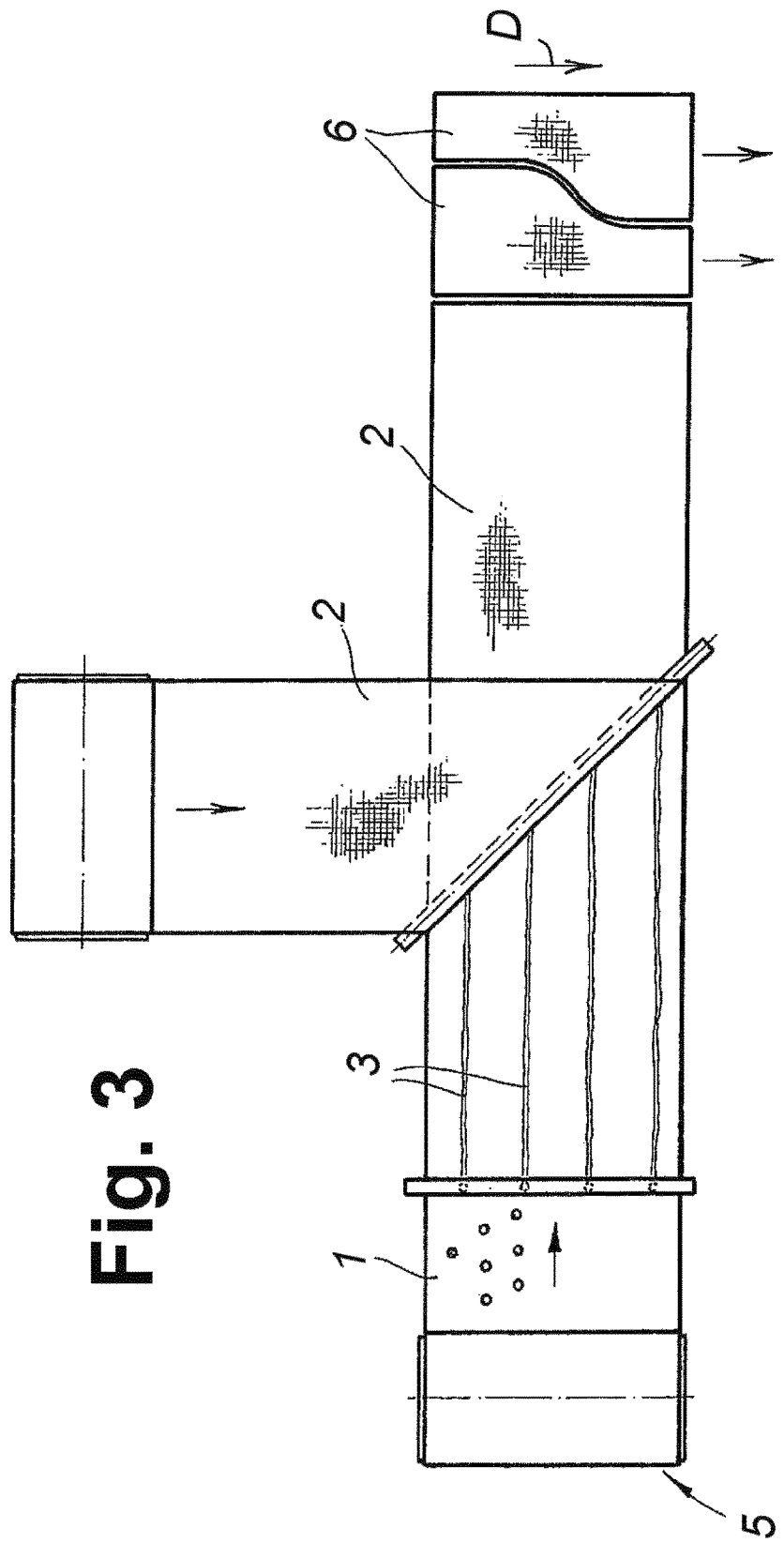

ELASTIC COMPOSITE TAPE

FIELD OF THE INVENTION

The present invention relates to an elastic composite tape. More particularly this invention concerns such a tape used at the sides of diapers and disposable pull-ups and a method making same.

BACKGROUND OF THE INVENTION

The invention relates to an elastic composite material for making elastic sides of diapers and of elastic diaper closure tapes, with an elastic substrate that can preferably stretch in one direction and with at least one textile outer layer consisting of a knit fabric. In order to ensure a good fitting shape of the diaper, elastic sides in diapers or elastic diaper closure tapes must have high elasticity and be able to stretch by more than 20 mm for the cited applications. Since they can come in contact with the body, they should be air permeable and have a soft textile surface. Finally, a high resistance to tearing of the elastic composite material is required for the cited applications.

U.S. Pat. No. 5,762,623 teaches a composite material comprising a first textile outer layer of a knit fabric, a second outer layer of spun fabric and an elastic substrate as core. The substrate consists of individual elastic threads extending in the high-stretch direction of the composite material. The threads are embedded in a suitable binder that fills out the space between the threads and also partially penetrates the outer textile layers. The binder is not air-permeable and therefore does not meet an important criterion for the previously cited applications.

US 2004/0214494 describes a composite material for diapers that comprises textile outer layers as well as an elastic core consisting of two layers. The outer layers can consist of a knit fabric. The core also comprises a layer of a knit fabric as well as comprises elastic threads extending in the high-stretch direction of the material. The elastic threads are cast in a suitable binder that fills out the hollow spaces between the outer layers and also partially permeates the outer layers. The textile layer of the core is intended to improve the composite strength and the adhesion between the individual layers. The elastic threads are cast in the binder in the extended state. The compound material is also not permeable to air.

U.S. Pat. No. 4,705,710 teaches a biaxially stretchable composite material with knitted-in loops that can be used as part of a Velcro strip fastener. The knit fabric comprises elements of an elastically stretchable material and is applied on an elastic substrate. Due to its biaxial stretchability the material is not suitable for the production of elastic sides for diapers or for the production of elastic diaper closure tapes because a composite material is required for these applications that can be stretched uniaxially and is relatively stiff transversely to the high-stretch direction so that the material does not contract transversely to the stretch direction upon a longitudinal expansion.

OBJECTS OF THE INVENTION

It is therefore an object of the present invention to provide an improved elastic composite tape.

Another object is the provision of such an improved elastic composite tape that overcomes the above-given disadvantages, in particular that is suitable for making elastic sides for diapers and elastic diaper closure tapes that can be stretched uniaxially, has good stretchability and a high resistance to tearing, and has a soft textile surface.

A further object is to provide an improved method of making such a tape.

SUMMARY OF THE INVENTION

An elastic composite tape has according to the invention a longitudinally elongated elastic generally planar substrate that can stretch greatly longitudinally and not stretch significantly transversely in its plane, at least one outer knit textile layer, and adhesive adhering the outer layer to the substrate strip.

Thus the material used as a diaper side or closure strap according to the invention has an elastic substrate that consists of a generally planar or flat material that has a high-stretch direction and is adhered to the knit fabric.

The knit fabric gives a fluffy surface to the composite material in accordance with the invention. It is characterized by a high permeability to air and good stretchability. The elastic substrate gives the desired elasticity in the desired direction to the composite material and determines the elastic return forces necessary for the described applications. The elastic substrate preferably consists of an air-permeable material. In principle, all adhesives used for laminated foils are suitable for adhering the substrate and the outer textile layer. Fusion adhesives based on aliphatic, primary alpha olefins APAO, EVA, styrene block polymers such as SBS, SEBS or SIS, reactive polyurethane adhesives, acrylate adhesives as well as radiation-hardening adhesives are preferred. The thickness of the applied adhesive is selected for the application of adhesive in such a manner that the yarns of the knit fabric are permanently anchored in the adhesive.

The adhesive for connecting the substrate to the knit fabric is advantageously applied in a pattern composed of adhesive zones and zones free of adhesive. The adhesive preferably forms a pattern of parallel lines aligned transversely to the high-stretch direction of the substrate. Since the adhesive is not applied as a continuous film and the adhesive zones do not have any substantial expansion in the high-stretch direction but rather preferably extend as strips or lines transversely to the stretch direction, the adhesive is not exposed to any substantial strain during a stretching of the composite material and does not prevent the stretching of the knitted fabric and of the elastic substrate.

The elastic substrate preferably consists of a single-layer or multilayer perforated foil that can comprise an elastomeric core layer and nonelastomeric cover layers, e.g., polyolefin cover layers as coextrudate. The perforation of the foil consists of air holes with diameters of 0.5 to 2 μm that can be produced by hot needle rollers.

It is also within the scope of the invention that the elastic substrate has a layer consisting of an elastic spun fabric that engages the knit fabric and can preferably stretch in the stretch direction of the substrate, and consists of filaments that comprise a filament core of a thermoplastic elastomer and a filament jacket of a nonelastic thermoplastic polymer that is stretched by the stretching of the spun fabric. The textile character of the composite material can be reinforced more by the use of an elastic substrate that is formed as a textile material or at least comprises a layer of a textile material bordering on the knit fabric. Furthermore, the elastic spun fabric is characterized as substrate material in that it can be stretched in accordance with the preliminary stretching of the filaments with a slight force up to a distinctly perceivable stretch limit. When the stretch limit of the material is reached a sharp rise of the force required for the further stretching can be noticed, so that an overstretching of the composite material due to improper use is largely excluded. Similar properties develop when the elastic substrate consists of a uniaxially elastic composite material that comprises a perforated elastic substrate foil of a thermoplastic elastomer as well as layers of an elastic spun fabric laminated on one or both faces.

In all previously described designs the knit fabric is preferably a warp knit fabric that has a high stretching capacity in the high-stretch direction of the composite material and is stiff or relatively nonstretchy in the transverse direction. The knit fabric can be manufactured from monofilament yarns or multifilament yarns and the filament yarns can consist, for example, of a polyamide, polyester, polypropylene, wool or cotton.

According to a preferred embodiment of the invention the outer layer consisting of a knit fabric on both faces of the elastic substrate and the preferred knit fabric is a warp knit fabric that can readily stretch in the stretch direction of the composite material and has a great resistance to stretching transversely to it.

The elastic substrate can have a shorter length than the outer layers. The outer layers are directly connected to each other in this instance on their projecting edges. The nonelastic foil can also be laminated in, if necessary, in the projecting regions.

The outside knit fabric of the composite material in accordance with the invention preferably has a weight per unit area between 15 and 50 g/m². The layer thickness of the elastic, flat substrate is preferably in a range between 20 and 100 μm.

The composite material in accordance with the invention can be elastically stretched in the high-stretch direction by 50% to 150%, during which permanent deformation after several stress-relieving cycles is at most 15%. The stretching force necessary for a stretching of 50% relative to a sample of 50 μm is preferably between 2 to 4 N/50 mm and the stretching force necessary for a stretching of 100% is 5 to 8 N/50 mm. The composite material in accordance with the invention is further characterized by a high resistance to tearing of more than 25 N/50 mm in the high-stretch direction.

The composite material in accordance with the invention is especially suitable for making elastic diaper closures that are used in the form of anatomically suitable side panels or tapes provided with closures in baby diapers and incontinence products for adults. The soft textile surface of the warp knit fabric ensures pleasant contact with the skin.

BRIEF DESCRIPTION OF THE DRAWING

The above and other objects, features, and advantages will become more readily apparent from the following description, reference being made to the accompanying drawing in which:

FIG. 3 is a schematic top view of a system for making the tape of this invention.

SPECIFIC DESCRIPTION

Figure 1:
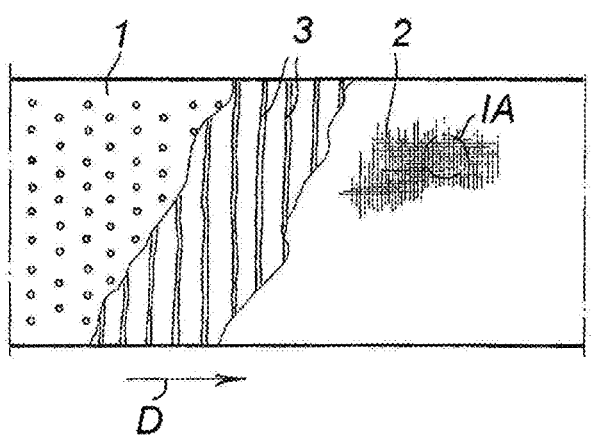
FIG. 1 is a top view of the composite material according to the invention.
Figure 1A:
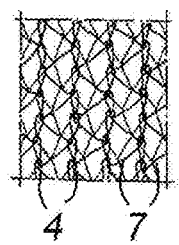
FIG. 1A is a large-scale view of the detail indicated at 1A in FIG. 1.
Figure 2:
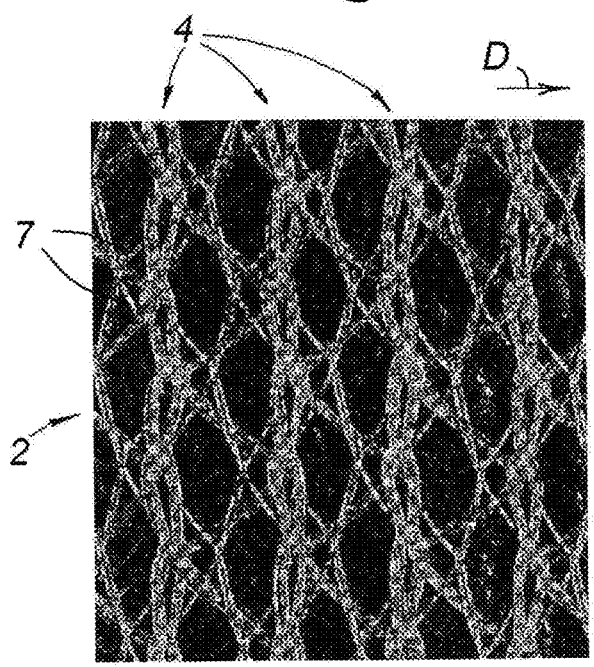
FIG. 2 is a much larger-scale view of the detail of FIG. 1A.

As seen in FIG. 1 an air-permeable tape 1 intended to stretch mainly in a longitudinal direction D has an elastic substrate strip 1 in the form of a perforated foil strip that is preferably stretchable the direction D. A textile outer layer consisting of a knit fabric 2 is laminated on both faces of the substrate 1. The knit fabric 2 is adhered to the elastic foil 1 by an adhesive is applied in a pattern composed of adhesive zones and adhesive-free zones. In the illustrated embodiment and according to a preferred embodiment of the invention the adhesive forms a pattern of parallel lines 3 aligned transversely to the preferred direction D of stretch of the substrate 1.

Figure 4:
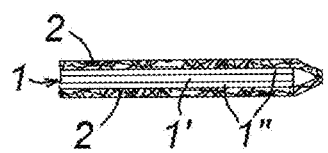
FIG. 4 is an edge view of an end of a tape according to the invention.

The knit fabric 2 is a warp knit fabric with knit warp chains 4 that can stretch only slightly in the direction of the warp but that is quite stretchy transversely, the chains 4 being interconnected by loose stretch weft filaments 7. The warp knit fabric 2 is produced from monofilament yarn or multifilament yarn consisting of polyamide, polyester, polypropylene, cotton, wool or other materials that can be handled with standard textile equipment. The warp knit fabric 2 has a weight per unit area between 15 and 50 g/m². The elastic substrate foil 1 advantageously has a layer thickness between 20 μm and 100 μm. In particular multilayer co-extrusion foils are suitable that have an elastic core 1' (FIG. 4) of a thermoplastic elastomer and have polyolefin cover layers 1". The soft knit outer layers 2 can extend past the elastic substrate core 1 and be laminated together.

The elastic substrate foil 1 as well as the warp knit fabric 2 used as outer layers have a high-stretch direction and are relatively nonstretchy in the transverse direction. This permits a production according to the laminating process shown in FIG. 3. Adhesive is applied on one face or both faces in the form of parallel lines 3 on the elastic substrate foil 1 that is pulled off a supply roll 5. Subsequently, the warp knit fabric strip 2 is laminated on one or both faces that is tension-proof in the machine direction (MD) shown in FIG. 3. Finally, elastic sides 6 for diapers are cut or stamped from the laminated composite that can elastically stretch transversely in the direction D that is perpendicular to the direction of the adhesive lines 3 and the process direction of the production machine.

We claim:

1. A uniaxially stretchable elastic composite tape comprising:
   a perforated, longitudinally elongated, elastic, and generally planar substrate foil that can stretch greatly longitudinally and not stretch significantly transversely in its plane;
   at least one outer warp-knit textile layer juxtaposed with the substrate foil and formed of transversely extending warp chains and longitudinally extending weft filaments, the weft filaments being loose such that the layer can stretch greatly longitudinally, the warp chains being relatively nonstretchable such that the layer cannot stretch significantly transversely; and
   adhesive adhering the outer knit textile layer to the substrate foil.

2. The elastic composite tape defined in claim 1 wherein the adhesive is in zones separated by adhesive free zones.

3. The elastic composite tape defined in claim 2 wherein the adhesive zones are thin, generally parallel, longitudinally spaced, and transversely extending strips.

4. The elastic composite tape defined in claim 1 wherein the foil comprises an elastic core layer and a pair of polyolefin cover layers between which the core layer is sandwiched.

5. The elastic composite tape defined in claim 1 wherein the knit layer is formed of yarns made of a polyamide, polyester, polypropylene, wool or cotton.

6. The elastic composite tape defined in claim 5 wherein there are two such outer knit textile layers between which the substrate foil is sandwiched.

7. The elastic composite tape defined in claim 6 wherein the outer layers extend past an outer edge of the substrate foil and are there laminated to each other.

8. The elastic composite tape defined in claim 1 wherein the outer warp-knit textile layer has a weight per unit area between 15 and 50 $g/m^2$ and that the elastic substrate foil has a thickness from 20 to 100 μm.

9. The elastic composite tape defined in claim 1 wherein the tape can be stretched longitudinally by 50% to 150%, has a permanent deformation after plural stretchings of at most 15%, and a resistance to longitudinal tearing of more than 25 N with a width of 50 mm.

10. A uniaxially stretchable elastic composite tape comprising:
- a perforated, longitudinally elongated, elastic, and generally planar substrate foil that can stretch greatly longitudinally and not stretch significantly transversely in its plane;
- two outer warp-knit textile layer sandwiching the substrate foil and each being able to stretch greatly longitudinally and not stretch significantly transversely, the warp-knit textile layers having ends extending longitudinally past the substrate foil and laminated together; and
- respective arrays of longitudinally spaced and transversely extending adhesive strips adhering the outer warp-knit textile layers to the substrate foil, the adhesive strips being separated by transversely extending adhesive-free zones.

* * * * *